(12) United States Patent
Yoneda

(10) Patent No.: US 10,400,206 B2
(45) Date of Patent: Sep. 3, 2019

(54) STERILE WORK SYSTEM

(71) Applicant: SHIBUYA CORPORATION, Kanazawa-shi, Ishikawa (JP)

(72) Inventor: Kenji Yoneda, Kanazawa (JP)

(73) Assignee: SHIBUYA CORPORATION, Kanazawa-shi, Ishikawa (JP)

( * ) Notice: Subject to any disclaimer, the term of this patent is extended or adjusted under 35 U.S.C. 154(b) by 483 days.

(21) Appl. No.: 15/030,179

(22) PCT Filed: Nov. 14, 2014

(86) PCT No.: PCT/JP2014/080159
§ 371 (c)(1),
(2) Date: Apr. 18, 2016

(87) PCT Pub. No.: WO2015/079930
PCT Pub. Date: Jun. 4, 2015

(65) Prior Publication Data
US 2016/0264921 A1    Sep. 15, 2016

(30) Foreign Application Priority Data

Nov. 26, 2013  (JP) ................................ 2013-243867

(51) Int. Cl.
| | |
|---|---|
| *C12M 1/12* | (2006.01) |
| *B01L 1/00* | (2006.01) |
| *B01L 1/04* | (2006.01) |
| *C12M 1/34* | (2006.01) |

(Continued)

(52) U.S. Cl.
CPC .............. *C12M 37/00* (2013.01); *B01L 1/00* (2013.01); *B01L 1/04* (2013.01); *C12M 41/46* (2013.01); *C12M 41/48* (2013.01); *F24F 3/16* (2013.01)

(58) Field of Classification Search
CPC . B01L 1/00; B01L 1/04; C12M 37/00; C12M 41/46; C12M 41/48; F24F 3/16
See application file for complete search history.

(56) References Cited

U.S. PATENT DOCUMENTS

2009/0161941 A1* 6/2009 Nakanishi .............. G06Q 10/00
382/141

FOREIGN PATENT DOCUMENTS

| JP | 3874304 B1 | 1/2007 |
|---|---|---|
| JP | 2007-185595 A | 7/2007 |
| JP | 2007-259799 A | 10/2007 |

(Continued)

OTHER PUBLICATIONS

International Search Report for PCT/JP2014/080159 (2 pgs.).

*Primary Examiner* — Shogo Sasaki
(74) *Attorney, Agent, or Firm* — Flynn Thiel, P.C.

(57) ABSTRACT

A sterile work can be applied by a worker 29 to cells or the like through a glove 28 provided in an isolator 15. A work headset 31 outputting a work procedure of the sterile work vocally is prepared for the worker, and a check input device 39 is prepared for a checker 36. A management device 12 outputs the work procedure of the sterile work this time vocally to the work headset. When the fact that the worker has normally performed the sterile work this time is checked by the checker, and when the fact is input from the check input device to the management device, the management device performs the subsequent work procedure. Since the sterile work by the worker 29 can be monitored by the checker 36, a wrong work can be prevented from being performed.

6 Claims, 3 Drawing Sheets

(51) Int. Cl.
    *C12M 1/36* (2006.01)
    *F24F 3/16* (2006.01)

(56) References Cited

FOREIGN PATENT DOCUMENTS

| | | |
|---|---|---|
| JP | 2007-260390 A | 10/2007 |
| JP | 2008-220316 A | 9/2008 |
| JP | 2010-233478 A | 10/2010 |
| JP | 2012-123768 A | 6/2012 |

* cited by examiner

STERILE WORK SYSTEM

TECHNICAL FIELD

The present invention relates to a sterile work apparatus and more specifically to a sterile work apparatus for performing a sterile work required for cultivation inside a sterile chamber as a sterile work space.

BACKGROUND ART

Conventionally, a sterile work system in which a sterile work required for cultivation is performed inside a sterile chamber as a sterile work space, such as a safety cabinet, a clean bench, an isolator and the like, is known (Patent Literature 1).

In the sterile system, a worker applies a sterile work according to a work procedure to cells or the like inside the safety cabinet and sequentially performs the work procedure of a series of the sterile works while checking that the work procedure is executed. More specifically, the sterile system includes a terminal device such as a work monitor for displaying the work procedure of the sterile work required for cultivation for the worker who performs the sterile work and also includes a foot switch for inputting that the work procedure has been normally executed.

A management device for managing the sterile work system causes the monitor to display the work procedure required this time, and the worker applies the work procedure this time to the cells or the like in accordance with the work procedure displayed on the monitor.

When the sterile work has been finished in accordance with the work procedure this time, the worker notifies the management device that the application of the work procedure has been finished through the foot switch.

Then, the management device displays the work procedure required next time on the monitor, whereby the worker performs the work procedure in accordance with the next work procedure.

PRIOR ART DOCUMENT

Patent Literature

Patent Literature 1 Japanese Patent No. 3874304

SUMMARY OF INVENTION

Problems to be Solved by the Invention

Conventionally, since the worker performing the work procedure and a checker who checks that the work has been finished are the same person, there is a problem that, if a wrong work procedure is performed, it is difficult to notice the error.

In view of such circumstances, the present invention provides a sterile work apparatus in which, if a wrong work procedure is performed, the error can be found easily.

Means for Solving the Problems

That is, the invention is a sterile work apparatus for performing a sterile work required for cultivation inside a sterile chamber as a sterile work space, including:

vocal output means for vocally outputting a work procedure of the sterile work required for cultivation for a worker performing the sterile work, a check input device for inputting a fact that the work procedure has been normally executed by a checker after checking whether or not the work procedure has been normally executed by the worker, and a management device for sending the work procedure to the work vocal output means and causing it to make a vocal output and for receiving a signal input into the check input device; and the management device sends the work procedure of the sterile work this time to the work vocal output means and causes the work vocal output means to vocally output the work procedure this time, and the management device further receives the fact that the work procedure this time has been normally executed from the check input device, sends the work procedure of the sterile work next time to the work vocal output means and repeats a series of these works.

Advantageous Effect of Invention

According to the aforementioned constitution, since the worker performing the sterile work and the checker checking whether or not the work procedure has been normally executed can be made separate, if the worker performs a wrong work procedure, the error can be found more easily by the checker.

MODE FOR CARRYING OUT THE INVENTION

Figure 1:
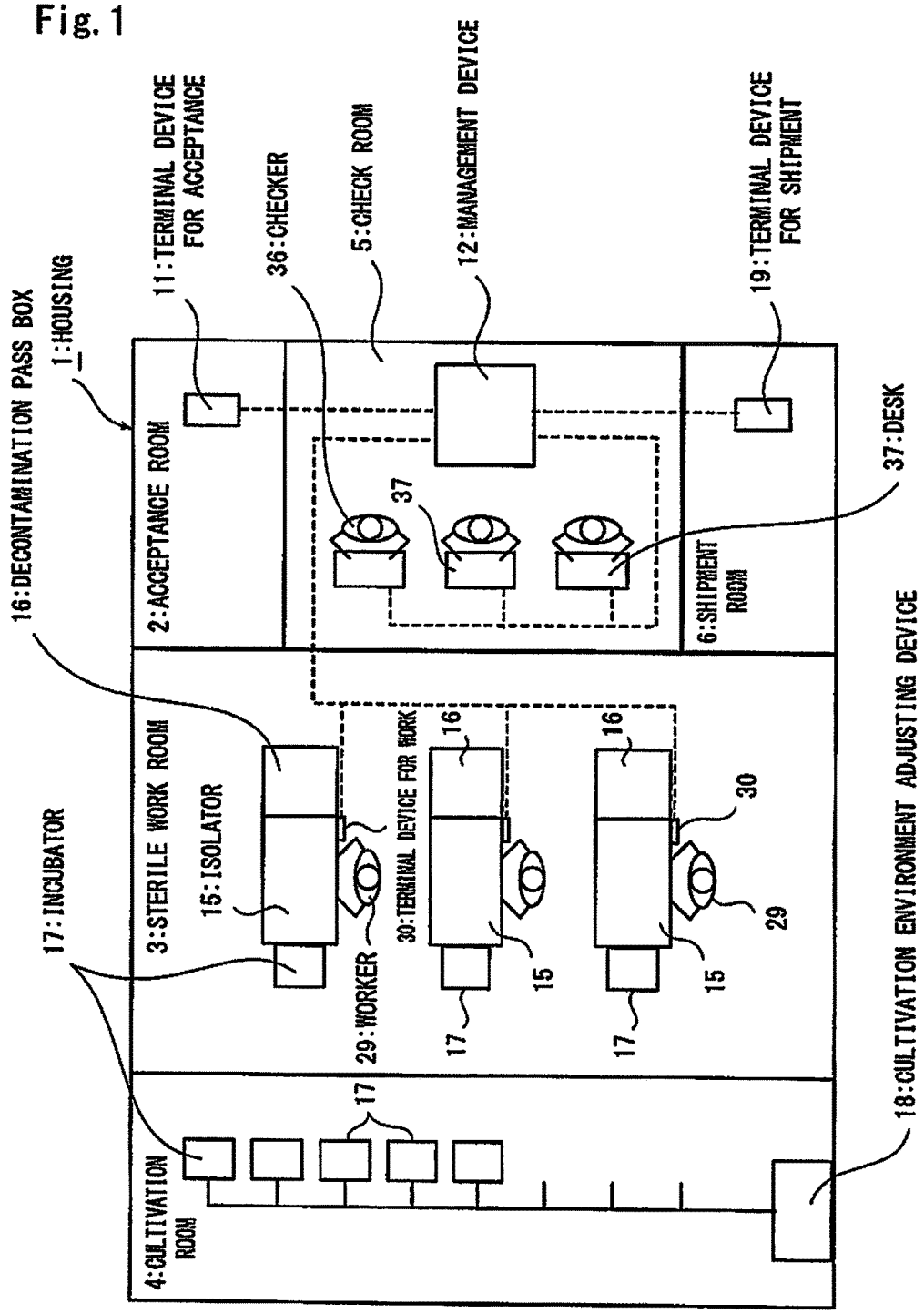
FIG. 1 is a schematic plan view illustrating a first embodiment of the present invention.

The present invention will be described below on the basis of illustrated embodiments, and in FIG. 1, an inside of a housing 1 of a culture facility is divided into an acceptance room 2, a sterile work room 3, a cultivation room 4, a check room 5, and a shipment room 6.

The acceptance room 2 is a room for accepting cells or tissues sampled from a human body by external medical institutions (including research institutions) and the cells or the like are contained in a sealed container, not shown, and carried into the acceptance room 2.

In the acceptance room 2, an acceptance terminal device 11 is provided, and required information on a cultivation target such as the time and date of sampling of the cell and the like is input into this acceptance terminal device 11. The information on the cultivation target before cultivation input into this acceptance terminal device 11 is transmitted to a management device 12 provided in a check room 5 and recorded therein. Moreover, in the management device 12, a schedule of cultivation corresponding to the cultivation target this time and a work procedure of the sterile work are set in advance.

In the sterile work room 3, a plurality of isolators 15 as sterile chambers, each formed having an inside as a sterile work space, are provided, while a decontamination pass box 16 is provided on one side of each of the isolators 15, while an incubator 17 is detachably attached to the other side.

In the decontamination pass box 16, the container containing the cells or the like, not shown, is constituted to be carried, and when the container is carried into the decontamination pass box 16, an internal space of the decontamination pass box 16 and an outer surface of the container are decontaminated. After that, the internal spaces of the isolator 15 and the decontamination pass box 16 are made to communicate with each other, and the cells or the like therein are introduced together with the container into the isolator 15.

The incubator 17 is connected to the isolator 15 with the inside of the incubator 17 kept in a sterile state, and the internal space of the isolator 15 and the internal space of the incubator 17 are made to communicate with each other. Then, as will be described later, the cells and the like to which a necessary sterile work required for cultivation was applied in the isolator 15 is divided into a plurality of cultivation containers from the container and transferred into the incubator 17 in a state contained in the cultivation containers and then, while the isolator 15 and the incubator 17 are connected to each other, the isolator 15 and the incubator 17 are sealed, respectively. After that, the incubator 17 is separated from the isolator 15.

The incubator 17 separated from the isolator 15 is carried into the cultivation room 4 and connected to a cultivation environment adjusting device 18 provided in the cultivation room 4, and the cultivation in the incubator 17 is continued.

A large number of the incubators 17 can be connected to the cultivation environment adjusting device 18, and while the cultivation environment in each of the incubators 17 is adjusted by the cultivation environment adjusting device 18, respective necessary cultivation is continued.

The cells or the like for which the necessary cultivation has been finished are taken into the isolator 15 from the incubator 17 and subjected to the required sterile work such as medium replacement, successive work and the like, and the cells or the like subjected to the sterile work are returned into the incubator 17 and connected to the cultivation environment adjusting device 18 in the cultivation room 4. Work records such as time and date of these performed works are input into a check input device 39 which will be described later, transmitted to the management device 12 and recorded as a progress of the work.

Then, the cultivation container containing the cells or the like for which all the cultivation has been finished is introduced into the decontamination pass box 16 from the incubator 17 through the isolator 15 and carried out to the shipment room 6 after an outer surface of the cultivation container is decontaminated in the decontamination pass box 16.

In the shipment room 6, a shipment terminal device 19 is provided, and to this shipment terminal device 19, information on the work record of the cultivation target and the like for which the cultivation has been completed is transmitted from the management device 12.

Then, when the cultivation container containing the cells or the like for which the cultivation has been completed is shipped, the shipment terminal device 19 is constituted to transmit the input information on the cultivation target after the cultivation to a management device of the medical institution to which the cultivation target is to be shipped.

Figure 2:
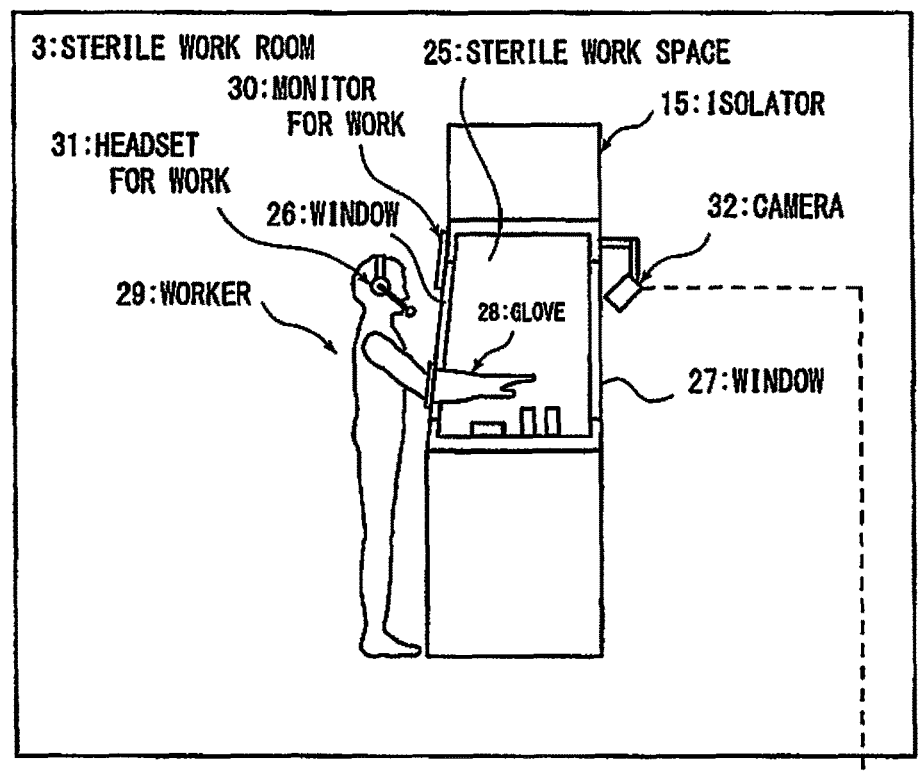
FIG. 2 is a partial sectional front view illustrating constitution inside a sterile work room 3 in FIG. 1.
Figure 2:
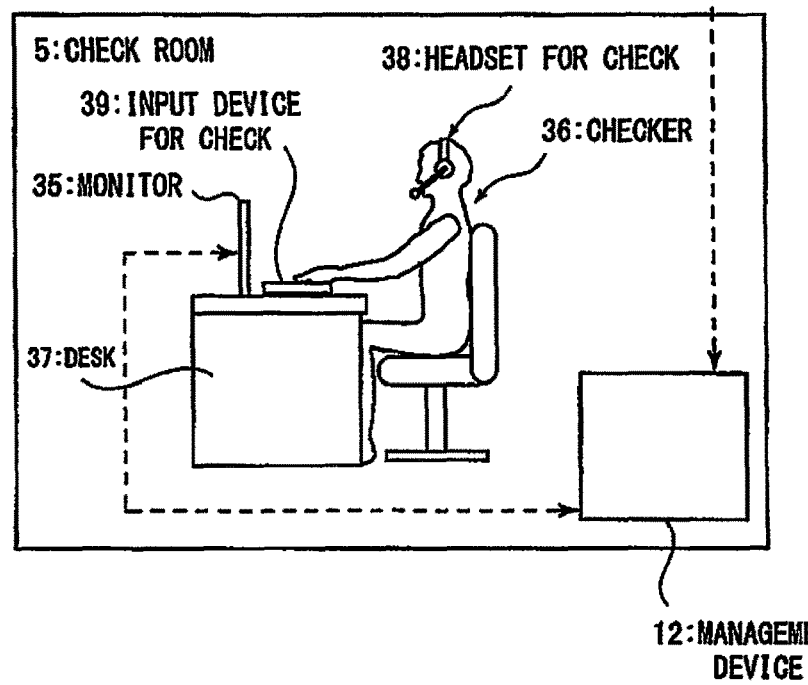

Each of the isolators 15 provided in the sterile work room 3 includes a sterile work space 25 shut off from the space in the sterile work room 3 as illustrated in FIG. 2 and is constituted such that the inside thereof can be seen through windows 26 and 27 provided on both surfaces of the isolator 15. The window 26 is provided on a front surface side of the isolator 15, and the window 27 is provided on a rear surface side.

A glove 28 is provided below the left window 26 in FIG. 2 so that a worker 29 can perform the sterile work required for cultivation in the isolator 15 while watching the inside of the isolator 15 through the window 26 from outside the isolator 15.

In the vicinity of the left window 26 in FIG. 2, a work monitor 30 as a work terminal device displaying the work procedure of the sterile work required for cultivation transmitted from the management device 12 is provided for the worker 29 performing the sterile work, and a work headset 31 as a vocal output means for vocally outputting the work procedure transmitted from the management device 12 is prepared for the worker 29.

A camera 32 is provided above the right window 27 in FIG. 2 so that the sterile work performed by the worker 29 in the isolator 15 can be photographed by the camera 32.

In the check room 5, monitors 35 in the same number as that of the cameras 32, that is, that of the isolators 15, are provided, and the cameras 32 and the monitors 35 are constituted to correspond to each other in a relation of 1:1. A video signal from each of the cameras 32 is output to the corresponding monitor 35 through the management device 12.

In the check room 5, a plurality of desks 37 are provided for a checker 36 who checks whether or not the work procedure has been normally executed by the worker 29. The monitor 35 is provided at each of the desks 37, and each of the checkers 36 can check whether or not each of the workers 29 has normally executed the work procedure by the video on the respective monitors 35.

Moreover, at each of the desks 35, a check headset 38 as a vocal output means for outputting vocally the same work procedure as that transmitted to the corresponding worker 29 is provided for each of the checkers 36, and a check input device 39 into which each of the checkers 36 inputs that the work procedure has been normally executed is provided. Though not shown, for the checker 36, a monitor as a terminal device for the checkers similar to the work monitor 30 may be provided so as to display the work procedure. Alternatively, the work procedure can be displayed with the video of the camera 32 on the monitor 35.

In the aforementioned constitution, when the cultivation target is accepted in the acceptance room 2, as described above, the information of the cultivation target this time is input into the management device 12 through the terminal device 11 for acceptance. The accepted cells or the like in the container are moved into the isolator 15 through the decontamination pass box 16 and further moved from inside the isolator 15 into the incubator 17 while being contained in the container as described above and are cultivated in the cultivation room 4.

The management device 12 specifies a work facility or a tool to be used in accordance with a set schedule and instructs the performance of the sterile work in the isolator 15.

The worker 29 decontaminates the container containing the cells or the like in the decontamination pass box 16 and then, moves it to the isolator 15 in accordance with the aforementioned instruction. Alternatively, the incubator 17 in the cultivation room 4 is connected to the isolator 15, and the cultivation container in the incubator 17 is moved to the isolator 15. Then, the worker 29 wears the work headset 31 and wears the glove 28 and then, notifies the fact to the checker 36 using a microphone of the work headset 31.

On the other hand, the checker 36 wears the checking headset 38 in the check room 5 and completes preparation of the sterile work while contacting with the worker 29 using a microphone of the checking headset 38. At this time, the worker 29 in the sterile work room 3 is required to wear a dustless outfit, but the checker 36 only needs to be in the check room 5 separate from the sterile work room 3 and thus, the checker 36 does not have to wear the dustless outfit that is worn in the sterile work room 3, and a burden on the checker 36 by wearing the dustless outfit can be reduced.

When the worker 29 in the sterile work room 3 and the checker 36 in the check room 5 have completed their respective preparation, the checker 36 instructs this fact to the management device 12 through the check input device 39.

As a result, the management device 12 transmits the first work procedure to the work monitor 30 to be displayed and transmits the work procedure to the work headset 31 and the check headset 38 and causes them to make vocal outputs. At this time, it is so configured that the work procedure, that is, sentences displayed on the work monitor 30 are automatically read out by using an OCR function of the management device 12 and vocally output to the work headset 31 and the check headset 38. Regarding the OCR function, the function of the work terminal device or the check terminal device may be used instead of that of the management device 12 itself. Alternatively, voice data created in correspondence with sentence data of the work procedure may be reproduced.

The worker 29 performs the first sterile work in the isolator 15 from outside the isolator 15 through the glove 28 in accordance with the work procedure using the voice output from the work headset 31, and the display on the work monitor 30.

This sterile work by the worker 29 is photographed by the camera 32, and the checker 36 monitors whether or not the sterile work has been normally performed in accordance with its work procedure by the monitor 35 while checking the work procedure vocally output by the check headset 38. Moreover, each time a predetermined process is completed, the checker 36 inputs the fact into the check input device 39 and causes the process to move to the subsequent one.

At this time, if the worker 29 wants to listen to the vocal output from the work headset 31 again, the worker can notify the fact to the checker 36 by using the microphone of the work headset 31, and the checker 36 can cause the work procedure to be output vocally again by instructing it to the management device 12 by using the check input device 39.

As described above, the worker 29 can concentrate on the sterile work without performing an input work to the management device 12 and can continuously monitor the sterile work performed by the worker 29 without taking his/her eyes off the monitor 35 by the vocal output from the check headset 38.

Therefore, the sterile work by the worker 29 and the check work by the checker 36 can be reliably performed, respectively.

When it is checked that the first work procedure has been normally executed, the checker 36 inputs the fact that the work procedure this time has been normally executed to the management device 12 from the check input device 39. As a result, the management device 12 saves the first work record and transmits the second work procedure to the work monitor 30, the work headset 31, and the check headset 38, and the worker 29 and the checker 36 perform the work similar to that described above on the basis of the second work procedure.

During the sterile work, if the work by the worker 29 is wrong, the checker 36 can tell it to the worker 29 through the microphone of the check headset 38 and can instruct a procedure to avoid the error.

Moreover, if the weight of the sampled cells or the like is to be measured, the checker 36 can perform a double-check by checking a measured value together with the worker 29 and thus, the checker 36 can input the measured value without an error in the check input device 39.

When the series of these works are repeated in the isolator 15 and all the work procedures are finished, the cells or the like in the isolator 15 are moved into the incubator 17, the incubator 17 separated from the isolator 15 is carried into the cultivation room 4 and connected to the cultivation environment adjusting device 18 so that the cultivation in the incubator 17 is continued. Alternatively, they are carried out to the space of the sterile work room 3 through the decontamination pass box 16.

In the aforementioned embodiment, the isolator 15 is used as a sterile chamber, but this is not limiting, and it is needless to say that a safety cabinet or a clean bench used in the aforementioned Patent Literature 1 can be used.

Moreover, in the first embodiment, the check room 5 is provided separately from the sterile work room 3 in which the worker 29 is working, but this is not limiting, and the check room 5 may be omitted.

Figure 3:
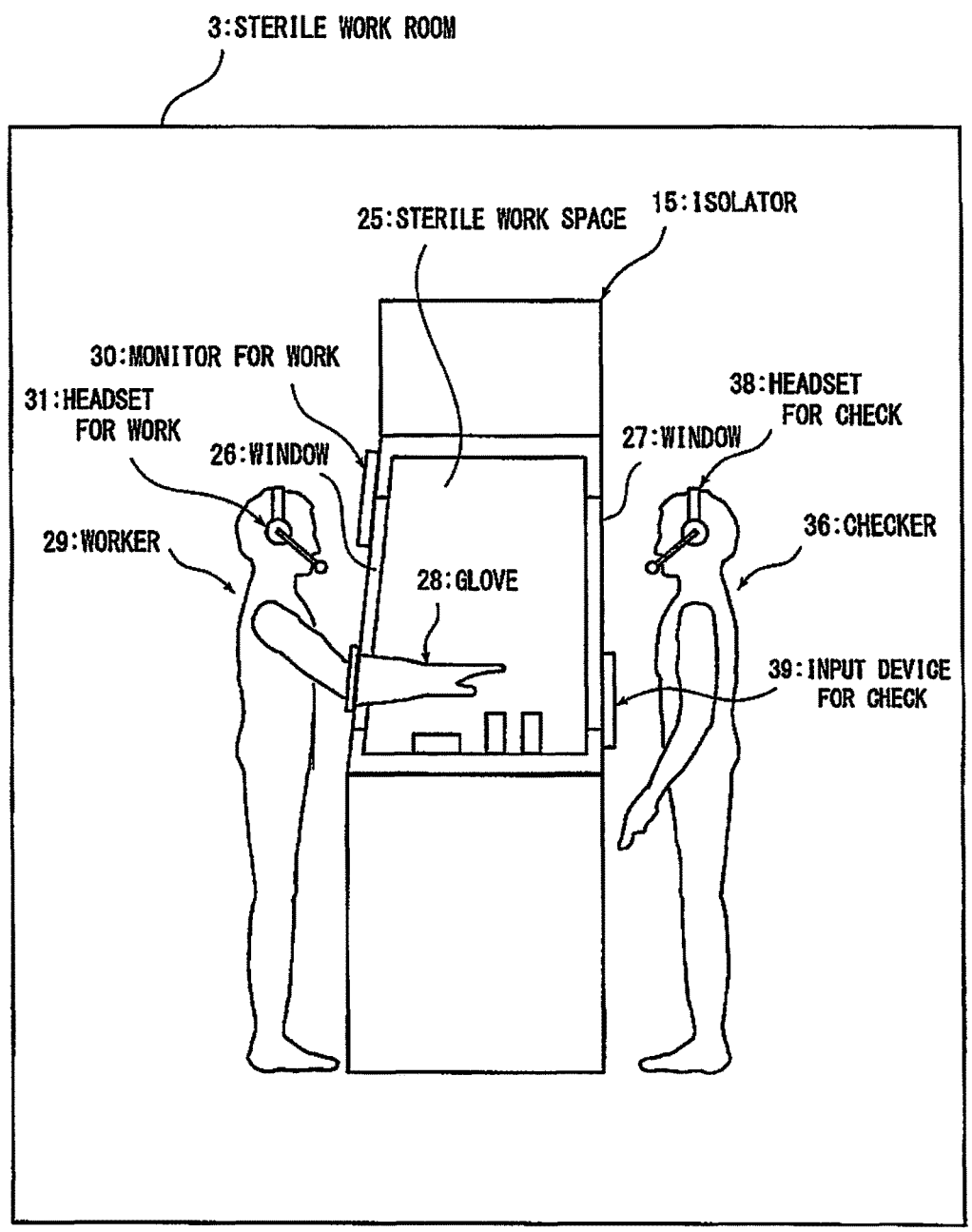
FIG. 3 is a partial sectional front view similar to FIG. 2 and illustrates a second embodiment of the present invention.

In this case, as illustrated in FIG. 3, it may be so constituted that the checker 36 enters into the sterile work room 3 together with the worker 29, wears the check headset 38 and directly monitors the sterile work performed by the worker 29 through the right window 27 in FIG. 3 provided in the isolator 15.

In this case, the camera 32 or the monitor 35 in the aforementioned first embodiment can be omitted, while the check input device 39 only needs to be provided in the vicinity of the right window 27 in FIG. 3. Alternatively, a display function may be provided in the check input device 39 so that the same work procedure as the work monitor 30 is displayed. In the second embodiment as above, too, monitoring of the work procedure by the worker 29 can be reliably performed similarly to the first embodiment.

The work monitor 30 displaying the work procedure or the check headset 38 for outputting the work procedure vocally may be omitted from each of the aforementioned embodiments, or a speaker may be employed as a work and check voice output means as necessary.

Reference Signs List 2 acceptance room
3 sterile work room
4 cultivation room
5 check room
6 shipment room
11 acceptance terminal device
12 management device
15 isolator (sterile chamber)
16 decontamination pass box
17 incubator
18 cultivation environment adjusting device
19 shipment terminal device
25 sterile work space
26, 27 window
29 worker
30 work monitor (work terminal device)
31 work headset (work vocal output means)
32 camera
35 monitor
36 checker
37 desk
38 check headset (check vocal output means)
39 check input device

The invention claimed is:

1. A sterile work apparatus for:
   enabling a worker to perform a sterile work required for cultivation inside a sterile chamber having an interior formed as a sterile work space; and enabling a checker to check whether or not the sterile work by the worker has been normally executed in accordance with a preset work procedure, comprising:
a headset for each of working and checking, which vocally outputs the work procedure for the worker and the checker;
a monitor for displaying the work procedure for the checker;
a checking input device for receiving input from the checker that the work procedure has been normally executed; and
a management device for transmitting and displaying the work procedure to and on the monitor, transmitting the work procedure to the headset for each of working and checking to automatically read out and vocally output at least part of the displayed work procedure, and receiving a signal input into the checking input device,
wherein the management device is configured to transmit and display a work procedure of current sterile work to and on the monitor, transmit the work procedure of current sterile work to the headset for each of working and checking vocally; and further, after reception of normal execution of the current work procedure of sterile work from the checking inputp device, transmit a work procedure of a subsequent sterile work to the monitor and transmit the work procedure or the subsequent sterile work to the headset for each of working and checking repeatedly.

2. The sterile work apparatus according to claim 1, additionally comprising:
a camera for photographing the sterile work performed by the worker inside the sterile chamber and a monitor for displaying a video photographed by the camera for the checker wherein the checker can check whether or not the work procedure has been normally executed by the worker on the basis of the video of the monitor.

3. The sterile work apparatus according to claim 2, wherein
the sterile work apparatus includes a sterile work room and a checking room;
the sterile chamber, the headset for working and a camera are installed in the sterile work room; and
the headset for checking, the checking input device and the monitor are provided in the checking room separate from the sterile work room.

4. The sterile work apparatus according to claim 3, wherein
a plurality of sets, each set including the sterile chamber, the headset for working and the camera, are provided in the sterile work room, while, in correspondence with the plurality of sets in the sterile work room, a plurality of sets, each set including the headset for checking, the checking input device and the monitor, are provided in the checking room, and a work procedure of the sterile work required for cultivation can be performed individually in each set.

5. The sterile work apparatus according to claim 1, additionally comprising:
an acceptance terminal device for receiving an input of information on a cultivation target before cultivation and for transmitting the input information on the cultivation target before cultivation to the management device is provided, wherein the management device records a progress of the work on the basis of the inputs into the acceptance terminal device and the checking input device.

6. The sterile work apparatus according to claim 1, additionally comprising:
a shipment terminal device into which information on the cultivation target for which all the work procedures of the sterile work required for the cultivation target have been finished and the cultivation has been completed is input from the management device is provided, wherein the shipment terminal device transmits the input information on the cultivation target after cultivation to a management device provided in a medical institution to which the cultivation target is shipped.

* * * * *